United States Patent

Gitzel et al.

[11] Patent Number: 5,055,619
[45] Date of Patent: Oct. 8, 1991

[54] PHOSPHONIUM COMPOUNDS AND PROCESSES FOR THEIR PREPARATION

[75] Inventors: Jörg Gitzel, Hattersheim am Main; Hans-Tobias Macholdt, Darmstadt; Wolfgang Knaup, Burgkirchen, all of Fed. Rep. of Germany

[73] Assignee: Hoechst Aktiengesellschaft, Frankfurt am Main, Fed. Rep. of Germany

[21] Appl. No.: 508,858

[22] Filed: Apr. 12, 1990

[30] Foreign Application Priority Data

Apr. 15, 1989 [DE] Fed. Rep. of Germany ....... 3912395

[51] Int. Cl.$^5$ .............................. C07F 9/02; C07F 5/02
[52] U.S. Cl. ........................................... 568/2; 568/9
[58] Field of Search ........................................ 568/2, 9

[56] References Cited

U.S. PATENT DOCUMENTS 4,422,975 12/1983 Mitchell ......................... 260/448 D

FOREIGN PATENT DOCUMENTS 2132893 6/1987 Japan ..................................... 568/2

OTHER PUBLICATIONS

Escoula, B. et al., *J. Chem. Soc. Chem. Commun* 1984:1233–34.

*Primary Examiner*—Jose G. Dees
*Assistant Examiner*—Porfirio Nazario

[57] ABSTRACT

Phosphonium compounds of formula (I):

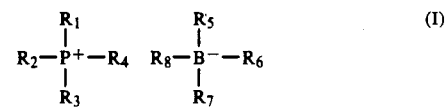

in which at least one of the radicals $R_1$ to $R_4$ is a fluorine-substituted, saturated alkyl radical having 1 to 30 carbon atoms and 3 to 50 fluorine atoms, which can contain further substituents, or at least one of the radicals $R_1$ to $R_4$ is a fluorine-substituted aryl radical or an aralkyl radical substituted by fluorine on the aromatic ring, it being possible for the aryl or aralkyl radical to be further substituted on the aromatic ring, and the alkyl bridge between the phosphorus atom and the aromatic ring, in the case of an aralkyl radical, containing 1 to 30 carbon atoms, and at most three of the radicals $R_1$ to $R_4$ independently of the others are hydrogen atoms, unsaturated or saturated, substituted or unsubstituted $C_1$–$C_{30}$ alkyl radicals or aryl or aralkyl radicals which can be substituted on the aromatic ring, and $R_5$ to $R_8$ are aryl radicals, aralkyl radicals or halogenoaryl radicals, and their preparation by reacting compounds of formula (II):

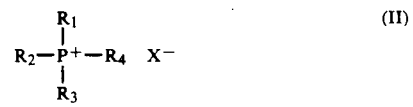

in which $R_1$ to $R_4$ are as defined and $X^-$ is a halogen anion, with a borate salt, in water or mixtures of water and an organic solvent, at about 20° C. to about 90° C.

5 Claims, No Drawings

PHOSPHONIUM COMPOUNDS AND PROCESSES FOR THEIR PREPARATION

DESCRIPTION

The present invention relates to novel phosphonium compounds and to processes for their preparation.

The present invention relates specifically to novel phosphonium compounds of general formula (I):

$$\begin{array}{cc} R_1 & R_5 \\ | & | \\ R_2-P^+-R_4 \quad R_8-B^--R_6 \\ | & | \\ R_3 & R_7 \end{array}$$

in which at least one of the radicals $R_1$ to $R_4$ is a linear or branched, fluorine-substituted, saturated alkyl radical having 1 to 30 carbon atoms and 3 to 50 fluorine atoms, which can contain further halogen atoms such as fluorine, chlorine, bromine or iodine atoms, and hydroxyl and/or chloromethyl and/or carboxamide and/or sulfonamide and/or urethane and/or keto and/or amino and/or $R_9-O-R_{10}$ groups, wherein $R_9$ and $R_{10}$ are $C_1-C_{30}$ alkyl radicals, or at least one of the radicals $R_1$ to $R_4$ is a fluorine-substituted aryl radical, for example a fluorine-substituted phenyl, toluyl or naphthyl radical, or an aralkyl radical substituted by fluorine on the aromatic ring, for example a fluorine-substituted benzyl radical, it being possible for the aryl or aralkyl radical to be further substituted on the aromatic ring by saturated or unsaturated, linear or branched $C_1-C_{30}$ alkyl, $C_1-C_{30}$ alkoxy, $C_1-C_{30}$ halogenoalkyl, $C_1-C_{30}$ halogenoalkoxy or hydroxyl groups or by halogen atoms such as fluorine, chlorine, bromine or iodine atoms, and the alkyl bridge between the phosphorus atom and the aromatic ring, in the case of an aralkyl radical, containing 1 to 30 carbon atoms, and at most three of the radicals $R_1$ to $R_4$ independently of the others are hydrogen atoms, linear or branched, unsaturated or saturated, substituted or unsubstituted alkyl radicals having 1 to 30 carbon atoms, or aryl or aralkyl radicals, for example phenyl, toluyl, naphthyl or benzyl radicals, which can be substituted on the aromatic ring by $C_1-C_{30}$ alkyl, $C_1-C_{30}$ alkoxy, $C_1-C_{30}$ halogenoalkyl, $C_1-C_{30}$ halogenoalkoxy or hydroxyl groups or by halogen atoms such as fluorine, chlorine, bromine or iodine atoms, and $R_5$ to $R_8$ are aryl radicals, for example phenyl, toluyl or naphthyl radicals, aralkyl radicals, for example the benzyl radical, or halogenoaryl radicals, for example fluorophenyl or chlorophenyl radicals, and to mixtures of these compounds.

The invention relates in particular to compounds of the abovementioned general formula (I) in which at least one of the radicals $R_1$ to $R_4$ is a linear or branched, fluorine-substituted, saturated alkyl radical having 4 to 17 carbon atoms and 3 to 25 fluorine atoms, which can contain further halogen atoms such as fluorine, chlorine, bromine or iodine atoms, and hydroxyl and/or chloromethyl and/or keto and/or $R_9-O-R_{10}$ groups in which $R_9$ and $R_{10}$ are $C_1-C_{18}$ alkyl radicals, or at least one of the radicals $R_1$ to $R_4$ is a fluorine-substituted aryl radical, for example a fluorine-substituted phenyl radical, or an aralkyl radical substituted by fluorine on the aromatic ring, for example a fluorine-substituted benzyl radical, it being possible for the aryl or aralkyl radical to be further substituted on the aromatic ring by saturated or unsaturated, linear or branched $C_1-C_{18}$ alkyl, $C_1-C_{18}$ alkoxy, $C_1-C_{18}$ halogenoalkyl, $C_1-C_{18}$ halogenoalkoxy or hydroxyl groups or by further halogen atoms such as fluorine, chlorine, bromine or iodine atoms, and the alkyl bridge between the phosphorus atom and the aromatic ring, in the case of an aralkyl radical, containing 1 to 18 carbon atoms, and at most three of the radicals $R_1$ to $R_4$ independently of the others are hydrogen atoms, linear or branched, unsaturated or saturated, substituted or unsubstituted alkyl radicals having 1 to 18 carbon atoms, or aryl or aralkyl radicals, such as phenyl, naphthyl or benzyl radicals, which can be substituted on the aromatic ring by $C_1-C_{18}$ alkyl, $C_1-C_{18}$ alkoxy, $C_1-C_{18}$ halogenoalkyl, $C_1-C_{18}$ halogenoalkoxy or hydroxyl groups or by halogen atoms such as fluorine, chlorine, bromine or iodine atoms, and $R_5$ to $R_8$ are phenyl, p-toluyl, p-chlorophenyl or naphthyl radicals, and to mixtures of these compounds.

The invention relates most especially to compounds of the abovementioned general formula (I) in which at least one of the radicals $R_1$ to $R_4$ is the group $-CH_2-CH_2-C_8F_{17}$ or $-CH_2-CH_2-Rf$ (where $Rf=C_6F_{13}$ to $C_{11}F_{23}$), and at most three of the radicals $R_2$ to $R_4$ are a phenyl radical, and the radicals $R_5$ to $R_8$ are phenyl, p-toluyl, p-chlorophenyl or naphthyl radicals, and to mixtures of these compounds.

The following may be mentioned as examples of individual compounds or mixtures of compounds of general formula (I):

| | | |
|---|---|---|
| $C_8F_{17}-CH_2-CH_2-\overset{-}{P}(phenyl)_3$ | $B(phenyl)_4^-$ | (1) |
| $C_8F_{17}-CH_2-CH_2-\overset{-}{P}(phenyl)_3$ | $B(p\text{-toluyl})_4^-$ | (2) |
| $C_8F_{17}-CH_2-CH_2-\overset{-}{P}(phenyl)_3$ | $B(p\text{-chlorophenyl})_4^-$ | (3) |
| $Rf-CH_2-CH_2-\overset{-}{P}(phenyl)_3$ <br> ($Rf = C_6F_{13}$ to $C_{11}F_{23}$) | $B(phenyl)_4^-$ | (4) |
| $Rf-CH_2-CH_2-\overset{-}{P}(phenyl)_3$ <br> ($Rf = C_6F_{13}$ to $C_{11}F_{23}$) | $B(p\text{-toluyl})_4^-$ | (5) |
| $Rf-CH_2-CH_2-\overset{-}{P}(phenyl)_3$ <br> ($Rf = C_6F_{13}$ to $C_{11}F_{23}$) | $B(p\text{-chlorophenyl})_4^-$ | (6) |
| 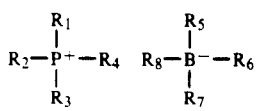 | $B(phenyl)_4^-$ | (7) |
| 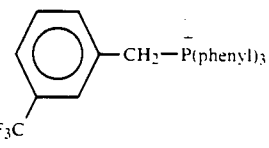 | $B(p\text{-toluyl})_4^-$ | (8) |
| 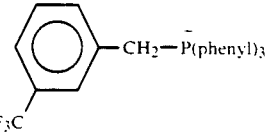 | $B(p\text{-chlorophenyl})_4^-$ | (9) |

$$F_3C\diagdown CF-\langle\bigcirc\rangle-CH_2-\overset{+}{P}(phenyl)_3 \quad B(phenyl)_4^- \quad (10)$$

$$F_3C\diagdown CF-\langle\bigcirc\rangle-CH_2-\overset{+}{P}(phenyl)_3 \quad B(p\text{-toluyl})_4^- \quad (11)$$

$$F_3C\diagdown CF-\langle\bigcirc\rangle-CH_2-\overset{+}{P}(phenyl)_3 \quad B(p\text{-chlorophenyl})_4^- \quad (12)$$

The phosphonium compounds and mixtures of phosphonium compounds of said general formula (I) can be prepared by reacting the phosphonium compounds and mixtures of phosphonium compounds of general formula (II):

$$R_2-\overset{R_1}{\underset{R_3}{\overset{+}{P}}}-R_4 \quad X^- \quad (II)$$

in which at least one of the radicals $R_1$ to $R_4$ is a linear or branched, fluorine-substituted, saturated alkyl radical having 1 to 30 carbon atoms and 3 to 50 fluorine atoms, which can contain further halogen atoms such as fluorine, chlorine, bromine or iodine atoms, and hydroxyl and/or chloromethyl and/or carboxamide and/or sulfonamide and/or urethane and/or keto and/or amino and/or $R_9$—O—$R_{10}$ groups, wherein $R_9$ and $R_{10}$ are $C_1$-$C_{30}$ alkyl radicals, or at least one of the radicals $R_1$ to $R_4$ is a fluorine-substituted aryl radical, for example a fluorine-substituted phenyl, toluyl or naphthyl radical, or an aralkyl radical substituted by fluorine on the aromatic ring, for example a fluorine-substituted benzyl radical, it being possible for the aryl or aralkyl radical to be further substituted on the aromatic ring by saturated or unsaturated, linear or branched $C_1$-$C_{30}$ alkyl, $C_1$-$C_{30}$ alkoxy, $C_1$-$C_{30}$ halogenoalkyl, $C_1$-$C_{30}$ halogenoalkoxy or hydroxyl groups or by halogen atoms such as fluorine, chlorine, bromine or iodine atoms, and the alkyl bridge between the phosphorus atom and the aromatic ring, in the case of an aralkyl radical, containing 1 to 30 carbon atoms, and at most three of the radicals $R_1$ to $R_4$ independently of the others are hydrogen atoms, linear or branched, unsaturated or saturated, substituted or unsubstituted alkyl radicals having 1 to 30 carbon atoms, or aryl or aralkyl radicals, for example phenyl, toluyl, naphthyl or benzyl radicals, which can be substituted on the aromatic ring by $C_1$-$C_{30}$ alkyl, $C_1$-$C_{30}$ alkoxy, $C_1$-$C_{30}$ halogenoalkyl, $C_1$-$C_{30}$ halogenoalkoxy or hydroxyl groups or by halogen atoms such as fluorine, chlorine, bromine or iodine atoms, and the anion X is a halogen anion, for example a chlorine, bromine or iodine anion, with a borate salt, in water or mixtures of water and an organic solvent such as isopropanol, isobutanol or methyl isobutyl ketone, at temperatures from about 20° C. to about 90° C., preferably from about 50° C. to about 80° C.

The compounds and mixtures of compounds of general formula (I) are obtained in good yield and purity and can be isolated direct from the reaction medium by filtration.

The synthesis of the compounds of said general formula (II) is described for example in J. Chem. Soc., Chem. Commun. 1984, 1233-34, Chem Ber. 114 (1981), 3589-3598, J. Fluorine Chem. 23 (1983), 339 and German Offenlegungsschrift DE-OS 29 36 211.

Thus, for example, the aforementioned compounds (1) to (6) are prepared by reacting the starting compounds (13) and (14) below with sodium tetraphenylborate, sodium tetra-p-chlorophenylborate or sodium tetra-p-toluylborate (see Preparatory Examples 1 and 2 below). Sodium tetra-p-chlorophenylborate and sodium tetra-p-toluylborate were prepared by the method of H. Holzapfel and C. Richter, J. Prakt. Chem. 26 (1964), 15-23.

$$C_8F_{17}-CH_2-CH_2-\overset{+}{P}(phenyl)_3 \quad I^- \quad (13)$$

$$Rf-CH_2-CH_2-\overset{+}{P}(phenyl)_3 \quad I^- \quad (14)$$
$(Rf = C_6F_{13} \text{ to } C_{11}F_{23})$ The compounds of the abovementioned general formula (I) according to the invention are outstandingly suitable for use as charge control agents in electrophotographic toner and developers for electrophotographic recording processes.

The following Preparatory Examples will serve to illustrate the invention without implying a limitation.

PREPARATORY EXAMPLE 1

8.4 g (0.01 mol) of compound (13) (molecular weight 836, preparation described in J. Chem. Soc., Chem. Commun. 1984, 1233-34) are dissolved in 150 ml of water/isopropanol (1:1 vol/vol). 3.4 g (0.01 mol) of sodium tetraphenylborate are then added slowly, with stirring. The volume is then made up to 400 ml with water/isopropanol and the mixture is boiled for 30 minutes. The white precipitate obtained is filtered off hot with suction, washed with water/isopropanol and dried at 50° C. under vacuum.

Yield: 9.3 g (90.5% of theory) of compound (1).
Molecular weight: 1028.
Melting point: 169°-170° C.
Elemental analysis: calc. 60.7% C, 3.8% H, 3.0% P, 1.1% B. found 60.7% C, 3.7% H, 3.0% P, 0.9% B, 0.06% water.

$^1$H NMR (in DMSO-$d_6$): 2.58 (multiplet, 2 methylene H), 4.02 (multiplet, 2 methylene H), 7.00 (multiplet, 20 phenyl H of the tetraphenylborate ion), 7.83 (15 phenyl H of the phosphonium cation) ppm.

PREPARATORY EXAMPLE 2

To prepare compound (2), the procedure described in Preparatory Example 1 is followed, except that 4.0 g (0.01 mol) of sodium tetra-p-toluylborate are used instead of sodium tetraphenylborate.

Yield: 9.7 g (89.5% of theory) of compound (2).
Molecular weight: 1084.
Melting point: 189°-190° C.
Elemental analysis: calc. 62.0% C, 4.3% H, 2.9% P, 1.0% B found 62.1% C, 4.2% H, 2.4% P, 0.9% B, 0.07% water.

$^1$H NMR (in DMSO-$d_6$): 2.14 (singlet, 3 toluyl H), 2.60 (multiplet, 2 methylene H), 3.99 (multiplet, 2 methylene H), 6.88 (multiplet, 16 p-toluyl H), 7.82 (multiplet, 15 phenyl H of the phosphonium cation) ppm.

What is claimed is:

1. A phosphonium compound of general formula (I):

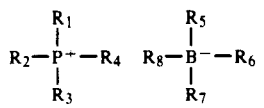

in which at least one of the radicals $R_1$ to $R_4$ is a linear or branched, fluorine-substituted, saturated alkyl radical having 1 to 30 carbon atoms and 3 to 50 fluorine atoms, which optional contains at least one further halogen atom and hydroxyl, chloromethyl, carboxamide, optionally at least one sulfonamide, urethane, keto, amino or $R_9$—O—$R_{10}$ group, wherein $R_9$ and $R_{10}$ are $C_1$-$C_{30}$ alkyl radicals, or at least one of the radicals $R_1$ to $R_4$ is a fluorine-substituted aryl radical or an aralkyl radical substituted by fluorine on the aromatic ring, the aryl or aralkyl radical optionally being further substituted on the aromatic ring by saturated or unsaturated, linear or branched $C_1$-$C_{30}$ alkyl, $C_1$-$C_{30}$ alkoxy, $C_1$-$C_{30}$ halogenoalkyl, $C_1$-$C_{30}$ halogenoalkoxy or hydroxyl groups or further halogen atoms, and the alkyl bridge between the phosphorus atom and the aromatic ring, in the case of an aralkyl radical, containing 1 to 30 carbon atoms, and at most three of the radicals $R_1$ to $R_4$ independently of the others are hydrogen atoms, linear or branched, unsaturated or saturated, substituted or unsubstituted alkyl radicals having 1 to 30 carbon atoms, or aryl or aralkyl radicals which are optionally substituted on the aromatic ring by $C_1$-$C_{30}$ alkyl, $C_1$-$C_{30}$ alkoxy, $C_1$-$C_{30}$ halogenoalkyl, $C_1$-$C_{30}$ halogenoalkoxy or hydroxyl groups or halogen atoms, and $R_5$ to $R_8$ are aryl radicals, aralkyl radicals or halogenoaryl radicals.

2. A compound of general formula (I) given in claim 1 in which at least one of the radicals $R_1$ to $R_4$ is a linear or branched, fluorine-substituted, saturated alkyl radical having 4 to 17 carbon atoms and 3 to 25 fluorine atoms, which contains at least one further halogen atom and optionally at least one hydroxyl, chloromethyl, keto or $R_9$—O—$R_{10}$ groups in which $R_9$ and $R_{10}$ are $C_1$-$C_{18}$ alkyl radicals, or at least one of the radicals $R_1$ to $R_4$ is a fluorine-substituted aryl radical or an aralkyl radical substituted by fluorine on the aromatic ring, the aryl or aralkyl radical optionally being further substituted on the aromatic ring by saturated or unsaturated, linear or branched $C_1$-$C_{18}$ alkyl, $C_1$-$C_{18}$ alkoxy, $C_1$-$C_{18}$ halogenoalkyl, $C_1$-$C_{18}$ halogenoalkoxy or hydroxyl groups or further halogen atoms, and the alkyl bridge between the phosphorus atom and the aromatic ring, in the case of an aralkyl radical, containing 1 to 18 carbon atoms, and at most three of the radicals $R_1$ to $R_4$ independently of the others are hydrogen atoms, linear or branched, unsaturated or saturated, substituted or unsubstituted alkyl radicals having 1 to 18 carbon atoms, or aryl or aralkyl radicals optionally substituted on the aromatic ring by $C_1$-$C_{18}$ alkyl, $C_1$-$C_{18}$ alkoxy, $C_1$-$C_{18}$ halogenoalkyl, $C_1$-$C_{18}$ halogenoalkoxy or hydroxyl groups or halogen atoms, and $R_5$ to $R_8$ are phenyl, p-toluyl, p-chlorophenyl or naphthyl radicals.

3. A compound of general formula (I) given in claim 1 in which at least one of the radicals $R_1$ to $R_4$ is the group —$CH_2$—$CH_2$—$C_8F_{17}$ or —$CH_2$—$CH_2$—Rf (where Rf=$C_6F_{13}$ to $C_{11}F_{23}$), and at most three of the radicals $R_2$ to $R_4$ are a phenyl radical, and the radicals $R_5$ to $R_8$ are phenyl, p-toluyl, p-chlorophenyl or naphthyl radicals.

4. The compound of the formula

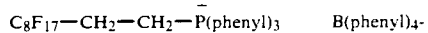

5. A compound or a mixture of compounds of the formula

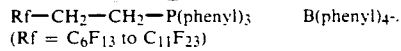

* * * * *